United States Patent [19]

Ouchi et al.

[11] 4,174,178
[45] Nov. 13, 1979

[54] BLOOD SERUM BEARING FILM WITH POSITION INDICATING MARK

[75] Inventors: Teruo Ouchi, Hachioji; Yutaka Kato, Tama, both of Japan

[73] Assignee: Olympus Optical Co., Ltd., Tokyo, Japan

[21] Appl. No.: 754,163

[22] Filed: Dec. 27, 1976

Related U.S. Application Data

[63] Continuation-in-part of Ser. No. 572,729, Apr. 29, 1975, abandoned.

[30] Foreign Application Priority Data

May 7, 1974 [JP] Japan ................................. 49/50423
Jun. 8, 1974 [JP] Japan ............................ 49/66532[U]
Sep. 4, 1974 [JP] Japan ................................ 49/100954

[51] Int. Cl.² ...................... G01N 33/16; G01N 21/16
[52] U.S. Cl. ....................................... 356/39; 356/244; 356/440
[58] Field of Search .................. 356/36, 39, 105, 244, 356/203, 344, 440; 23/253 R (U.S only)

[56] References Cited

U.S. PATENT DOCUMENTS

| 3,342,997 | 9/1967 | Taylor et al. | 356/203 |
| 3,695,762 | 10/1972 | Tylko et al. | 356/36 |
| 3,898,457 | 8/1975 | Packard et al. | 23/253 R |
| 3,907,503 | 9/1975 | Betts et al. | 23/253 R |
| 3,932,133 | 1/1976 | Ishikawa | 23/253 R |

Primary Examiner—Vincent P. McGraw
Attorney, Agent, or Firm—Ostrolenk, Faber, Gerb & Soffen

[57] ABSTRACT

A plurality of spaced blood serum samples are disposed on a serum-bearing film having a leading and trailing edge. The blood serum samples are disposed in an array and each blood serum sample has a leading and a trailing edge. A position-indicating mark is disposed forward of the leading edge of the sample closest to the leading edge of the film by a distance representative of the spacing between adjacent ones of the samples.

18 Claims, 18 Drawing Figures

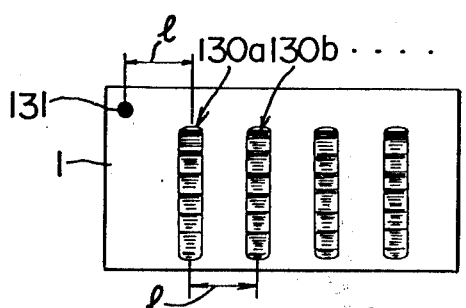
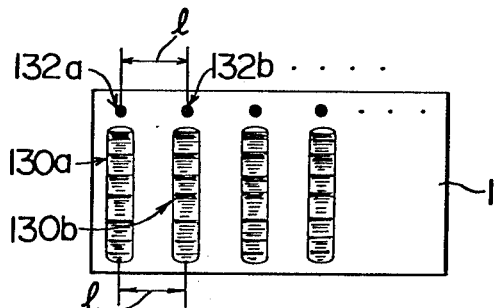
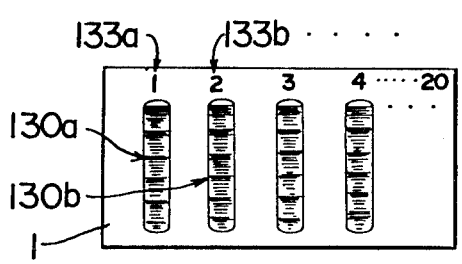
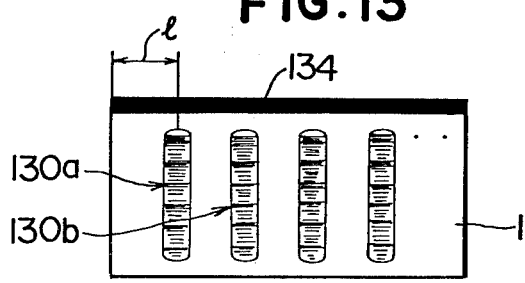
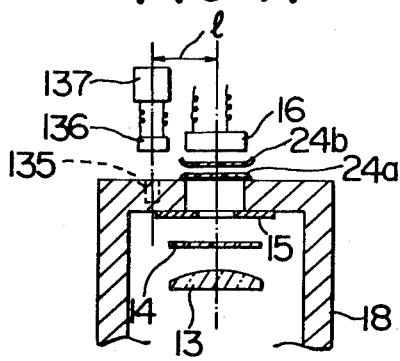
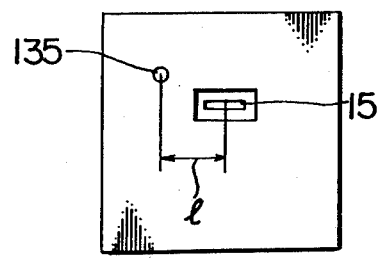
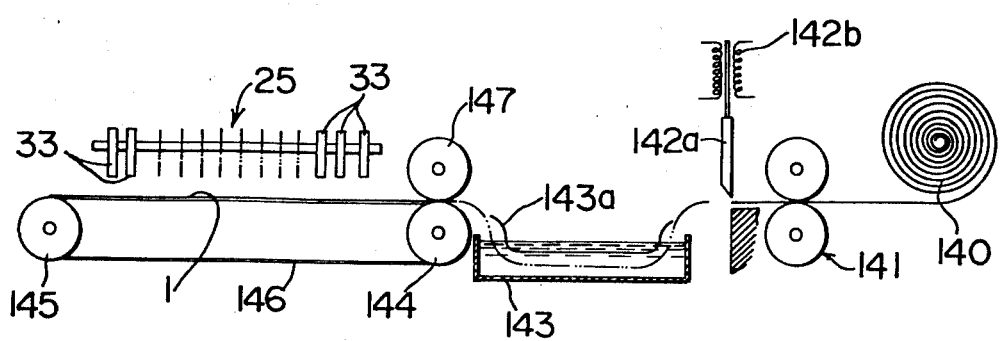

BLOOD SERUM BEARING FILM WITH POSITION INDICATING MARK

RELATED APPLICATIONS

This is a continuation-in-part of U.S. application Ser. No. 572,729 filed Apr. 29, 1975 and now abandoned.

BACKGROUND OF THE INVENTION

The present invention relates to a blood serum-bearing film and more particularly to a blood serum-bearing film which may be used in a blood serum analyzer of the cataphoresis type. In analyzers of the foregoing type, a blood serum applied to a bearing film is fractionated into components by cataphoresis and the fractions are measured by means of a densitometer or a filter photoelectric colorimeter for the purpose of quantitative analysis of the serum components.

Recently, much attention has been directed to a cataphoretic serum analyzer in view of the simple process of analysis and the reliability of the analytical results obtained. However, this process has been greatly dependent upon manual operations including individual analysis of each sample on a bearing film.

SUMMARY OF THE INVENTION

It is a primary object of the present invention to provide a blood serum-bearing film including a position-indicating mark which will enable automation of the analysis process. Two major embodiments are disclosed.

In the first embodiment, a plurality of blood serum samples are disposed on a serum-bearing film having a leading and a trailing edge. The samples are disposed in an array, each sample having a leading and a trailing edge. A position-indicating mark is disposed forward of the leading edge of the sample closest to the leading edge of the film by a distance representative of the spacing between adjacent ones of the samples.

In a second embodiment, a plurality of spaced blood serum samples are again disposed on a serum-bearing film in an array. In this embodiment, a plurality of position-indicating marks are provided, each position-indicating mark being indicative of the position of a different blood serum sample.

As a result of the foregoing structure, it is possible to utilize the disclosed blood serum-bearing film in an automatic apparatus for analyzing each of the plurality of blood serum samples disposed on the film.

BRIEF DESCRIPTION OF THE DRAWINGS

FIG. 10 to 13 are plan views of serum-bearing films provided with position indicating marks;

FIG. 14 is a cross section of a position detector;

FIG. 15 is a plan view of the position detector shown in FIG. 14;

FIG. 16 is a schematic side elevation of an apparatus for supplying a length of bearing film to the blood serum applicator apparatus from a roll thereof;

DETAILED DESCRIPTION OF THE PREFERRED EMBODIMENTS

Figure 17:
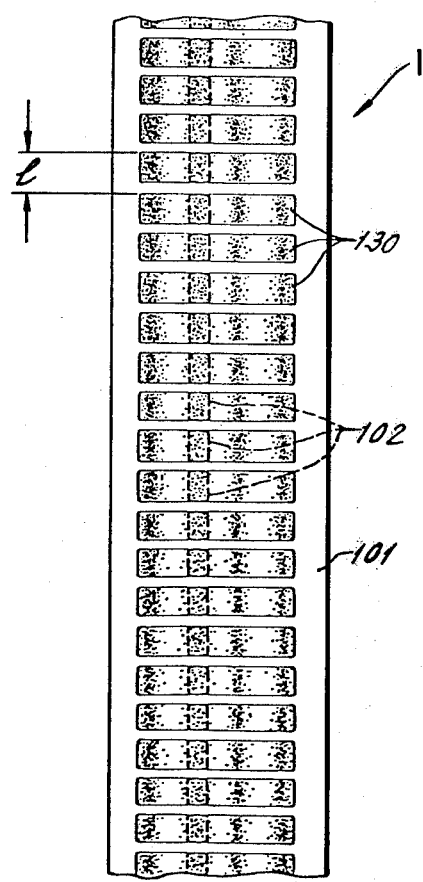
FIG. 17 is a top view of one example of a specimen film.

Referring now to the drawings wherein like numerals indicate like elements, there is shown in FIG. 17 one example of a specimen film 1. The specimen film 1 is generally produced by a series of steps including the following:

(1) a carrier film 101 which comprises cellulose acetate, is wetted with Veronal-Veronal sodium buffer solution.

(2) a blood serum 102 is applied to the carrier film in an evenly spaced array, the leading edge of each of the blood sample 102 being spaced from the leading edge of the adjacent blood sample by a distance 1.

Figure 18:
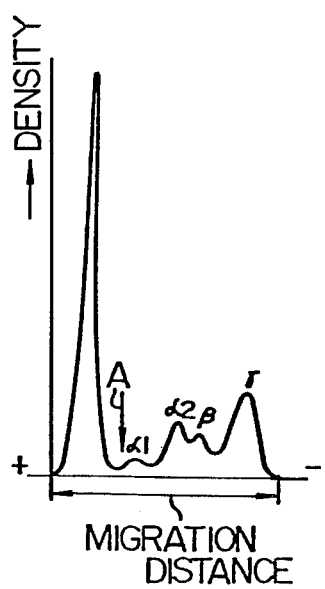
FIG. 18 graphically shows an exemplary density distribution of a typical fractionated pattern of the specimen.

(3) a pair of positive and negative electrodes are disposed on the opposite sides of the carrier film, as viewed crosswise thereof, and energized to effect a cataphoresis of the blood serum 102, which is caused to migrate to produce a fractionated pattern 130. The direction and distance of the migration of various components contained in the blood serum 102 vary depending upon their polarity, and FIG. 18 shows a typical distribution. In FIG. 18, the abscissa represents the distance of migration along the width of carrier film 101 and the ordinate the density, indicating a density distribution of fractionated components. The peak which is located closest to the ordinate represents the density of albumin which is formed toward the positive electrode relative to the position A where the blood serum is applied. Viewing from left to right, successive peaks designated by characters $\alpha_1$, $\alpha_2$, $\beta$ and $\gamma$ represent the density of corresponding globulin components, and are formed toward the negative electrode.

(4) the carrier film 101 having a fractionated pattern obtained by the cataphoresis of the serum components is dried and then decolorized, whereby only the fractionated pattern remains colorized to provide a specimen 130.

(5) the carrier film 101 having a number of specimens 130 form thereon and is dried to provide a specimen film 1.

The apparatus disclosed herein is directed to making the specimen film 1 thus obtained clear by treating it with a clearing liquid and determining the density of the fractionated pattern of respective specimens on the specimen film 1 as by colorimeter or densitometer.

Figure 1:
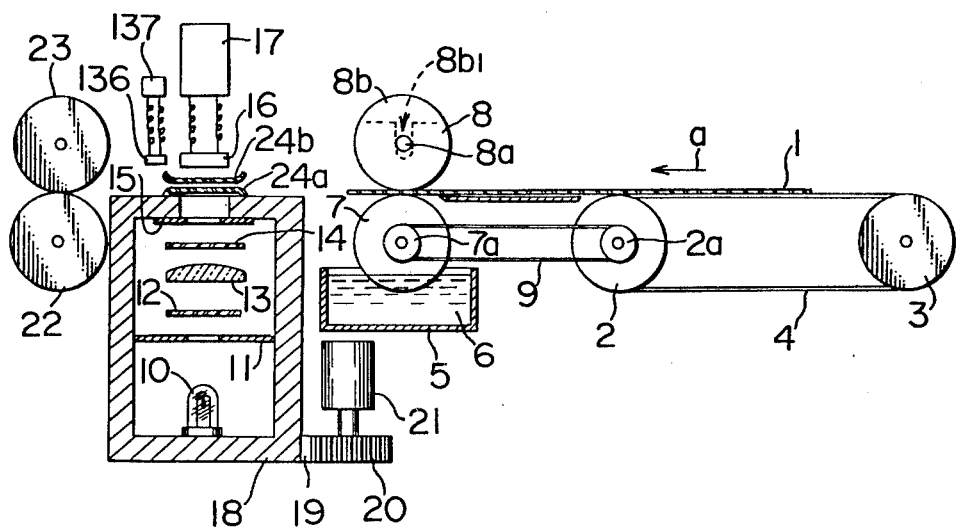
FIG. 1 is a schematic side elevation, partly in section, of a cataphoretic blood serum analyzer to which the invention is applied.

Now a cataphoretic blood serum analyzer to which the invention is applied will be described before going into further detail of the blood serum applicator apparatus according to the invention. Referring to FIG. 1, there is shown a blood serum bearing film 1 which has been subjected to the steps of energization for cataphoretic process, staining, decoloration and drying to form a specimen. A driver roller 2 is connected with a suitable power source (not shown) for rotation, and a driven roller 3 is spaced therefrom. A belt 4 is entrained around the pair of rollers 2, 3, and the film 1 is placed on the belt 4 for movement in the direction indicated by an arrow a. A vessel 5 for containing a liquid agent 6 such as liquid paraffin or Dekalin which makes the film clear is disposed to the left of the roller 2. An applicator roller 7 is disposed over the vessel 5 so as to be partly immersed in the liquid agent 6, and a cooperating roller 8 is disposed above the roller 7 so as to be in abutting relationship therewith. The roller 8 has its shaft 8a rotatably and slidably received in a recess 8b1 formed in a support wall 8b, so as to bear against the film 1 by gravity as the latter enters the nip between the rollers 7, 8. The roller 7 has a gear 7a coaxially fixed thereon, which is connected with a gear 2a coaxially secured to the drive roller 2 through a chain 9, whereby the rotation of the drive roller 2 is effective to rotate the roller 7. A photoelectric colorimeter includes a light source 10, a diaphragm 11, a heat-isolating filter 12, a condenser lens 13, a filter 14 which only permits the transmission of radiation of a particular wavelength, a slit member 15, a light receiving element 16 and a detector 17 connected therewith. All these components are housed in a casing 18, which has a rack 19 secured thereto for meshing engagement with a pinion 20, which is in turn rotated by a motor 21. A pair of feed rollers 22, 23 are disposed adjacent to the colorimeter.

As the drive roller 2 rotates, the bearing film 1 is conveyed in the direction of the arrow a, and is further conveyed to the left by the rollers 7, 8. Since the roller 7 is partly immersed in the liquid agent 6, the film 1 is made clear by the liquid agent as it is conveyed by the rollers 7, 8. The movement of the film 1 is interrupted by suitable means when the leading one of the test substances or serum samples on the film 1 has moved to the region between a pair of transparent plates 24a, 24b which are disposed on the optical axis of the optical system of the colorimeter. At the same time, the motor 21 is set in motion to move the casing 18 along a suitable guide in a direction perpendicular to the plane of the drawing, whereby the fractionated pattern of the serum on the film 1 will be scanned by the light from the light source to thereby provide a colorimetric quantitative determination of the fractionated pattern of the serum protein. Usually, film 1 which is made clear is secured in place between a pair of transparent plates before it is scanned by the colorimeter. However, since this aspect is not essential to the understanding of the present invention, it will not be described in detail. The test substances are spaced apart in an array lengthwise of the film 1 while the direction of the cataphoresis traverses across the film 1.

Figure 2:
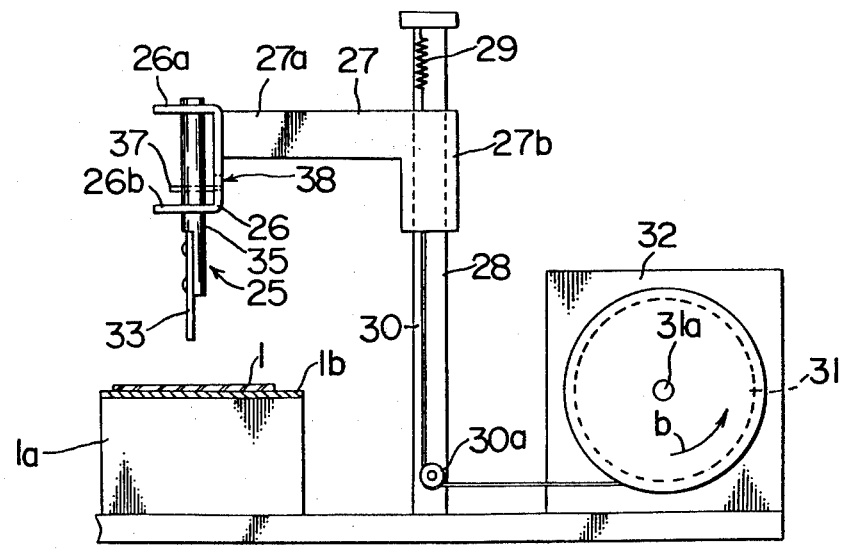
FIG. 2 is a side elevation of the blood serum applicator apparatus with which the film of the present invention may be used.
Figure 3:
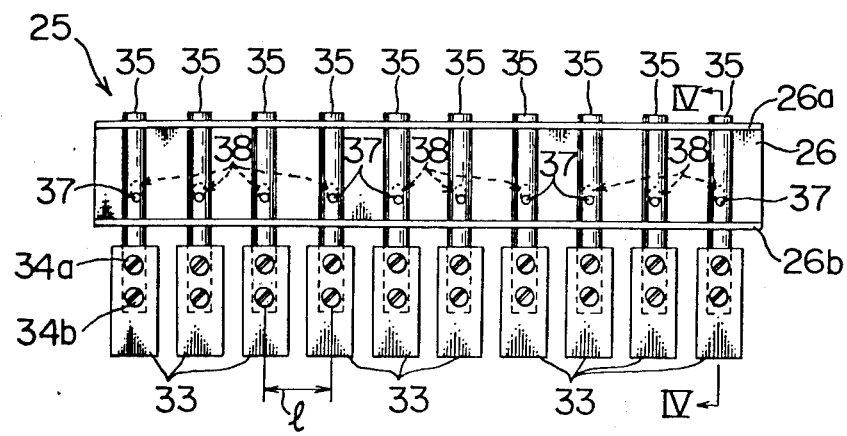
FIG. 3 is a front view of the applicator assembly, showing a plurality of applicator members attached to a support.
Figure 4:
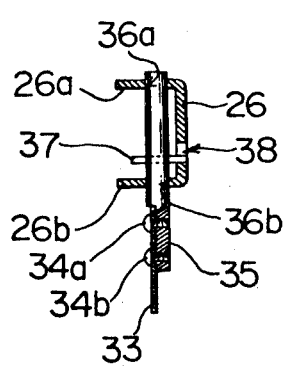
FIG. 4 is an elevational cross section taken along the line IV—IV shown in FIG. 3.
Figure 5:
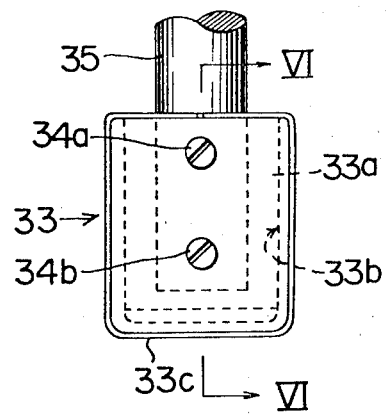
FIG. 5 is a front view of one applicator member.
Figure 6:
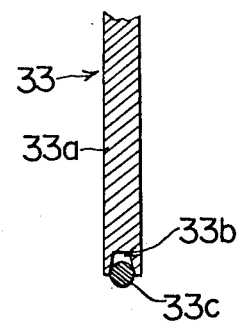
FIG. 6 is an elevational cross section taken along the line VI—VI shown in FIG. 5.

FIG. 2 shows the blood serum applicator apparatus according to the invention. The apparatus includes an applicator assembly 25 which comprises a plurality of applicator members (FIG. 3) carried by a channel member 26 having upper and lower limbs 26a, 26b. The channel member 26 is attached to one end 27a of a support arm 27, the other end 27b of which is slidably mounted on a post 28 and is connected with a spring 29 which extends between the support arm and an abutment at the top of the post. The bottom of the end 27b of the support arm 27 has one end of a wire 30 secured thereto, which extends around a pulley 30a pivotally mounted on the bottom of the post 28 and is connected with a drive wheel 31 at its other end. The drive wheel 31 has its shaft 31a coupled with a drive source 32 such as a motor for rotation in the direction indicated by an arrow b. A more detailed description of the applicator assembly 25 will be given with reference to FIGS. 3 to 6. As shown in FIGS. 5 and 6, an applicator member is generally shown at 33 and comprises a thin sheet 33a which is formed with an elongate groove 33b in the peripheral edge of at least its forward end, and a wire 33c is fitted into the groove 33b. The arrangement is such that the blood serum is permeated into the space between the groove 33b and the wire 33c by surface tension so as to achieve an adsorption of a fixed amount of serum. Each applicator member 33 is secured to a shank 35 by means of set screws 34a, 34b, and the shank 35 is slidably received in aligned openings 36a, 36b formed in the respective limbs of the channel member 26 (see FIG. 4). It will be seen from FIG. 3 that the openings are formed in the channel member at a constant spacing along its length. The portion of the shank 35 which extends between the limbs 26a, 26b has a pin 37 fixedly mounted thereon, which pin is loosely fitted in a slot 38 formed in the body of the channel member 26. In this manner, the applicator member 33 is vertically movable relative to the channel member 26 by the cooperation between the pins 37 and the slots 38.

In operation, when the applicator members 33 are in their raised position as shown in FIG. 2, the blood serum to be examined is applied to the tip of the respective applicator members 33 by suitable means. Subsequently, the drive source 32 is energized to rotate the drive wheel 31 in the direction indicated by the arrow b, whereupon the wire 30 is wound on the drive wheel 31 to pull the support arm 27 downward along the post 28 against the resilience of the spring 29. As the support arm 27 moves downward, the channel member 26, shanks 35 and applicator members 33 move downward as a unit until the applicator members 33 bear against the film 1 which is placed on a table 1a with a wet paper filter 1b interposed therebetween. As the support arm 27 further moves downward, the channel member 26 continues to move downward, but the applicator members 33 remain in position in which they bear against the film 1. When the channel member 26 has descended to a suitable position, suitable means such as a microswitch is used to deenergize the drive source 32, and then energized in the opposite direction to reverse the rotation of the drive wheel 31 or alternatively simply deenergized with a clutch between the motor and the shaft 31a deactuated, depending on the variety of the motor drive used. Thereupon, the support arm 27 is raised under the action of the spring 29, and therefore the channel member 26 secured thereto is also raised, ultimately accompanying the applicator members 33 to return to the start position shown in FIG. 2.

During such operation, the blood serum applied to the respective applicator members 33 will be uniformly applied to the film all at one time when they bear against the latter. To apply the blood serum to the respective applicator members 33, a serum receiver (not shown) having wells therein which are spaced apart from each other at the same spacing as the applicator members 33 may be brought into position on the table by a suitable feeding mechanism at the time when the blood serum applicator apparatus assumes the position shown in FIG. 2 or before its operation is initiated. The support arm 27 is lowered to apply the serum to the respective applicator members 33, and then raised. Subsequently, the receiver is removed from the table, and replaced by the film. In such an instance, it will be readily appreciated that the support arm 27 may be rotated on the post 28 to bring it into alignment with the serum receiver.

Figure 7:
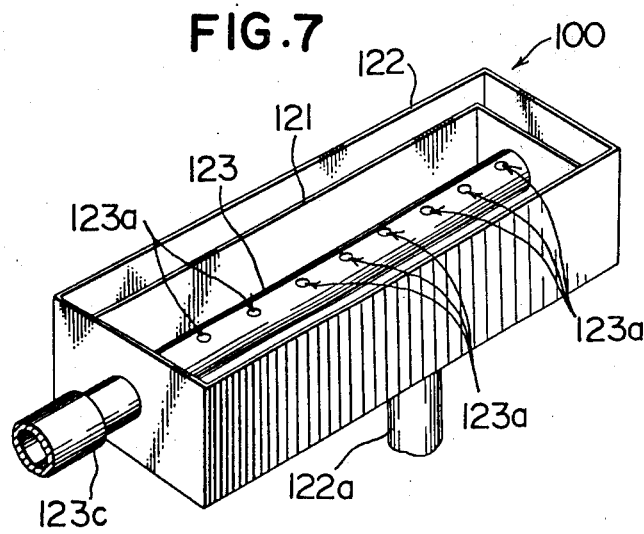
FIG. 7 is a perspective view of a cleaning unit.
Figure 8:
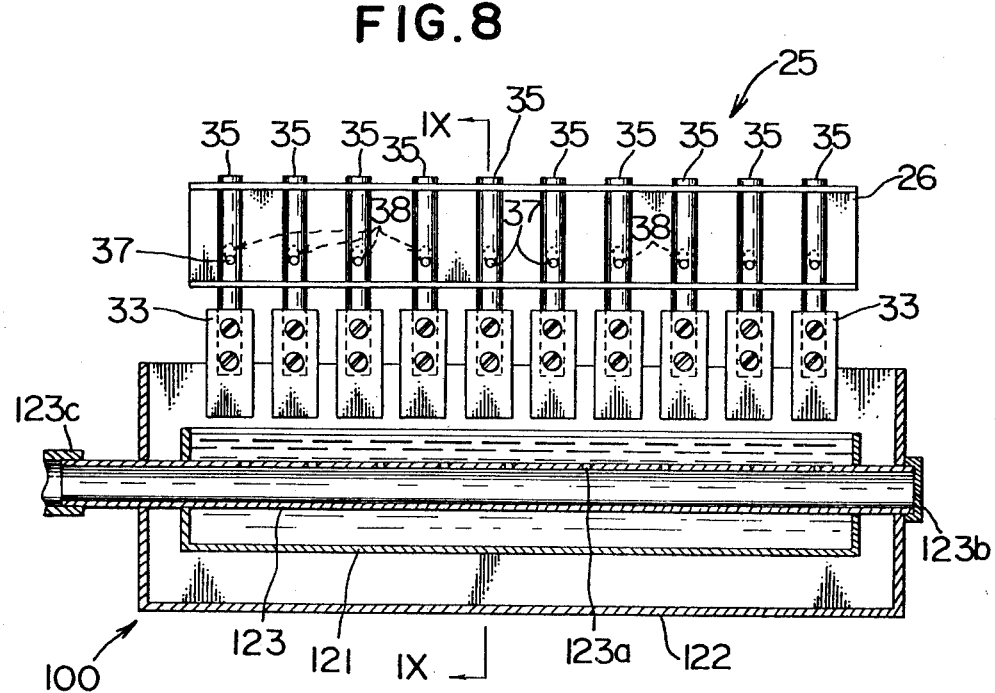
FIG. 8 is a front view, partly in section, of the cleaning unit shown in FIG. 7 and showing the applicator assembly of FIG. 3 employed in conjunction with the cleaning unit.
Figure 9:
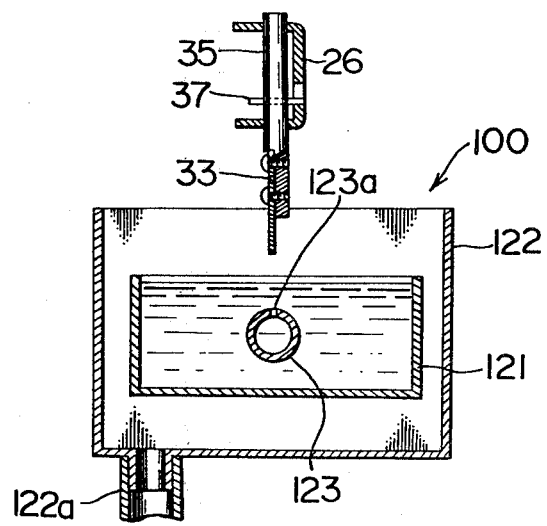
FIG. 9 is an elevational cross section taken along the line IX—IX shown in FIG. 8.

After application of the serum, the applicator members are cleaned free from the serum by a cleaning unit 100 shown in FIGS. 7 to 9. The unit 100 includes a vessel 121 for containing a cleaning solution, a second vessel 122 located outside the vessel 121 for accepting the cleaning solution discharged therefrom, and a pipe 123 which extends through the both vessels 121 and 122. At its top, the pipe 123 is formed with a plurality of apertures 123a. The pipe 123 is closed at its one end by sealing member 123b (see FIG. 8), and is connected with a connection tube 123c at its other end for injection of a cleaning solution such as tap water or the like. The vessel 122 is provided with a drainage tube 122a (see FIG. 9) in its bottom.

The cleaning unit 100 operates as follows:

Subsequent to the application of the serum which takes place by lowering the applicator members from the position shown in FIG. 2, the applicator assembly 25 is inserted into the vessel 121 (see FIG. 8). Assuming that the connection tube 123c is connected with a water line, the water will spout from the apertures 123a formed in the pipe 123 to form a flow in every direction, whereby the applicator members 33 disposed within the vessel 121 will be cleaned by such water flow. The water overflows to the outside vessel 122 and is drained through the drainage 122a. Thus, the water within the vessel 121 is maintained clean.

FIGS. 10 to 13 show position indicating marks 131, 132a, 132b..., 133a, 133b..., 134 applied on the film 1 in accordance with the constant spacing between the applicator members 33 of the blood serum applicator apparatus. For the films shown in each of these Figures, a blood serum is applied to the film 1 at a constant spacing l, fractionated by cataphoresis, followed by staining, decoloration and drying, thereby forming a fractionated pattern 130a, 130b...

In FIG. 10, a mark 131 is applied to the film 1 at a position which is by a distance l advanced or to the left of the leading fractionated pattern 130a. In FIG. 11, marks 132a, 132b... are aligned with the respective fractionated patterns 130a, 130b... FIG. 12 shows that the number of specimens, 133a, 133b..., are entered in alignment with the respective fractionated patterns 130a, 130b... FIG. 13 shows a band-shaped mark 134 of a fixed width applied along one lateral edge of the film 1.

A quantitative analysis by means of photoelectric colorimeter will be described for the use of a bearing film provided with marks as mentioned above. The cataphoretic serum analyzer shown in FIG. 1 includes a light emitting element 135 (see FIGS. 14 and 15) comprising a light emitting diode or the like which is positioned in the wall of the casing 18 below and to the left of the light receiving element 16. The light emitting element 135 is laterally spaced from the light receiving element 16 by a distance which is equal to the spacing l of serum applications, as measured between their optical axes. A light receiving element 136 is disposed above the light emitting element 135 for receiving light therefrom, and is connected with a detector 137. When the film 1 passes between the elements 135 and 136, the mark thereon is detected by the detector 137. For a film having one mark 131 shown in FIG. 10, the motion of the film conveying means such as the roller 7 can be interrupted and the motor 21 rotated when the film 1 has moved through a given length l after the detection signal is produced, thereby assuring correct alignment for scanning. Subsequently, the scanning is repeated at the given spacing so as to perform the quantitative analysis of every specimen.

For marks 132a, 132b... shown in FIG. 11, the light emitting diode 135 and the light receiving element 136 of the photoelectric colorimeter may be positioned in a corresponding manner. In this instance, each of the marks 132a, 132b... located laterally adjacent to each test substance or fractionated pattern is detected to stop the movement of the bearing film and to initiate the scanning of the fractionated pattern. This assures a scanning to be performed at a correct position even if the blood serum is not applied at an exact spacing.

FIG. 12 shows numerals entered as marks corresponding to the previous ones, which can be detected in the same manner as mentioned before. However, numerals indicated at 133a, 133b serve to distinguish by itself a plurality of test substances of the blood serum applied to a single bearing film 1.

FIG. 13 shows a mark 134 of a constant width applied to one lateral edge of the bearing film 1. When the bearing film 1 has advanced to a position such that its leading edge is located between the light emitting element 135 and the light receiving element 136, the mark can be immediately detected. In this instance, the blood serum is applied to the film at predetermined positions spaced from the leading edge thereof. To provide an example demonstrating this feature, reference is made to FIG. 16 which shows an apparatus for feeding a continuous bearing film. A bearing film is unreeled from a roll 140, and is successively passed through a pair of feed rollers 141, and a cutter 142a which cooperates with a drive electromagnet 142b to cut the film to a given length. Subsequently, the length of the film is passed through a vessel 143 containing an aqueous solution of Veronal-sodium Veronal, the film being guided against a guideplate 143a. Then the film is fed to a belt 146 which extends around a pair of spaced rollers 144 and 145. A squeegee roller 147 is disposed on the belt in opposing relationship with the roller 144 for removing an excess amount of the buffer solution. A serum applicator assembly 25 as shown in FIG. 2 is disposed over the upper run of the belt. When the length of the bearing film has advanced to a suitable position on the belt 146, the motion of the belt 146 is interrupted, and the serum applicator assembly 25 operated to apply a blood serum to given positions on the bearing film 1. Subsequently, the film 1 is fed by means not shown, into a cataphoretic apparatus which is then energized, followed by the steps of staining, decoloration, clearing and a quantitative analysis with a photoelectric colorimeter. By controlling the application of a blood serum such that a first test substance of the blood serum is spaced from the leading edge of the film 1 by a predetermined distance, a scanning at a correct position is assured wherever the film is cut by the cutter 142, without requiring marks to be inscribed on the film 1 concurrent with or after the application of the blood serum to the film.

With the examples shown in FIGS. 10 to 12, the cataphoretic apparatus must be provided with a marking device suitably located therein, but such a marking device may be located on a given position on the serum applicator assembly so that the film is marked concurrently with the application of the blood serum.

What is claimed is:

1. A blood serum-bearing film comprising:
   a serum-bearing film having a leading and a trailing edge;
   a plurality of equally spaced blood serum samples disposed on said film in an array, each said blood serum sample having a leading and a trailing edge; and
   a positive indicating mark disposed forward of the leading edge of the sample closest to said leading edge of said film by a distance representative of the spacing between adjacent ones of said samples.

2. A blood serum-bearing film as in claim 1, wherein said film is transparent.

3. A blood serum-bearing film as in claim 2, wherein said indicating mark is opaque.

4. A blood serum-bearing film as in claim 3, wherein said blood samples are translucent.

5. A blood serum-bearing film as in claim 2, wherein said film comprises cellulose acetate.

6. A blood serum-bearing film as in claim 1, wherein said blood samples are fractionated patterns obtained by the cataphoresis of the serum components.

7. A blood serum-bearing film, comprising:
   a serum-bearing film;
   a plurality of spaced blood serum samples disposed on said film in an array;
   a plurality of position-indicating marks, each said position-indicating mark being indicative of the position of a different said blood serum sample and comprising a different numeral.

8. A blood serum-bearing film as in claim 7, wherein each said position-indicating mark is aligned with the different said blood serum sample.

9. A blood serum-bearing film as in claim 7, wherein each of said blood serum samples are equally spaced apart.

10. A blood serum-bearing film as in claim 7, wherein said film is transparent.

11. A blood serum-bearing film as in claim 10, wherein each of said position-indicating marks is opaque.

12. A blood serum-bearing film as in claim 11, wherein said blood serum samples are translucent.

13. A blood serum-bearing film as in claim 7, wherein said film comprises cellulose acetate.

14. A blood serum-bearing film as in claim 7, wherein each of said blood serum samples are fractionated patterns obtained by the cataphoresis of the serum components.

15. A blood serum-bearing film as in claim 1 wherein said film has a lateral edge extending from said leading to said trailing edge and wherein said position indicating mark runs along the entire length of said lateral edge, said leading edge of said film being spaced from the leading edge of said sample closest to said leading edge of said film by said distance l.

16. A blood serum-bearing film, comprising:
   a serum bearing film;
   a plurality of blood serum samples disposed on said film in an array; each of said blood serum samples having a leading and a trailing edge, the leading edge of each of said blood serum samples being spaced from the leading edge of adjacent blood serum samples by a distance l as measured along a predetermined direction; and
   a position indicating mark disposed from the leading edge of one of said blood serum samples by said distance l as measured in said predetermined direction whereby, the distance between said position indicating mark and said leading edge of said one of said blood serum samples is representative of the spacing between adjacent ones of said blood serum samples.

17. The serum-bearing film of claim 16, wherein said serum bearing film has a leading edge and said position indicating mark is located forward of said leading edge of said blood serum sample closest to said forward edge of said film as measured in said predetermined direction.

18. A blood serum-bearing film as in claim 16 wherein said film has a lateral edge extending from said leading to said trailing edge and wherein said position indicating mark runs along the entire length of said lateral edge, said leading edge of said film being spaced from the leading edge of said sample closest to said leading edge of said film by said distance l.

* * * * *